United States Patent [19]

Colombo et al.

[11] Patent Number: 4,746,294

[45] Date of Patent: May 24, 1988

[54] CYLINDRICAL THREADED PIN FOR DENTAL PROSTHESIS IMPLANTATIONS

[76] Inventors: Domenico Colombo, Via Musa, 4, Como; Ugo Pasqualini, Via Borgonuovo, 26, Milano, both of Italy

[21] Appl. No.: 8,691

[22] Filed: Jan. 30, 1987

[30] Foreign Application Priority Data

Mar. 27, 1986 [IT] Italy ............................... 53199/86[U]

[51] Int. Cl.⁴ ............................................. A61C 8/00
[52] U.S. Cl. ..................................... 433/174; 433/221
[58] Field of Search ........................ 433/174, 221, 225

[56] References Cited

U.S. PATENT DOCUMENTS

| Re. 29,817 | 10/1978 | Lieb et al. | 433/221 |
| 3,449,830 | 6/1969 | Weissman | 433/225 |
| 3,579,830 | 5/1971 | Morel | 433/174 |
| 3,905,109 | 9/1975 | Cohen et al. | 433/174 |
| 4,365,958 | 12/1982 | Vlock | 433/225 |
| 4,468,200 | 8/1984 | Münch | 433/174 |

FOREIGN PATENT DOCUMENTS 2143609 2/1985 United Kingdom ............... 433/225

*Primary Examiner*—Paul J. Hirsch
*Assistant Examiner*—Adriene J. Lepiane
*Attorney, Agent, or Firm*—Cullen, Sloman, Cantor, Grauer, Scott, & Rutherford

[57] ABSTRACT

A threaded pin for implantation use in dentistry, comprising a cylindrical stem with an external thread near one end, a head for application of a tool at the other end and a point at the opposite end near the thread. The point has the same shape as the point of the milling cutter used to make the elongated hole in the bone in which the implantation is to be make. The dimensions of the thread are relatively small in comparison with the diameter of the stem to avoid exerting excessive pressure and cause damage to the bone as the pin is screwed thereinto.

3 Claims, 1 Drawing Sheet

U.S. Patent May 24, 1988 4,746,294
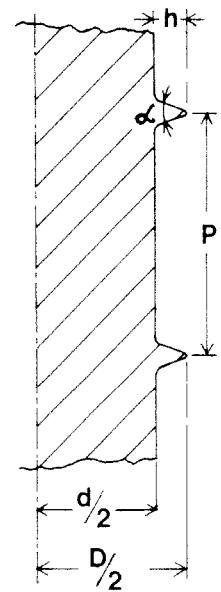
FIG. 4
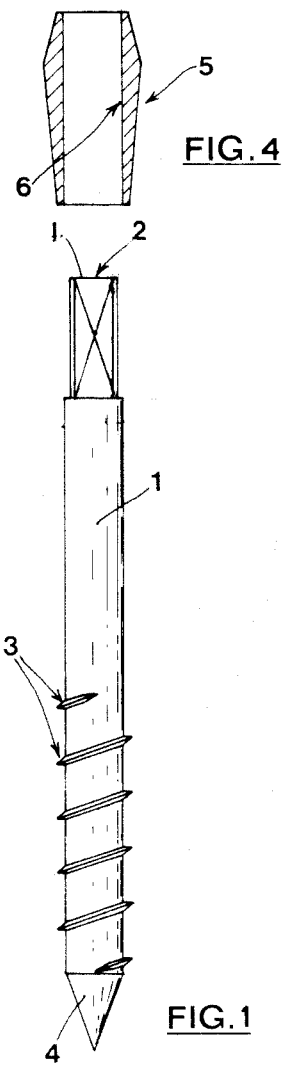
FIG. 1
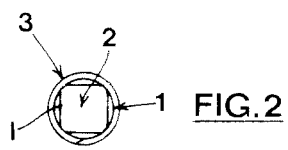
FIG. 3
FIG. 2

CYLINDRICAL THREADED PIN FOR DENTAL PROSTHESIS IMPLANTATIONS

BACKGROUND OF THE INVENTION

This invention relates to a cylindrical threaded pin for dental prosthesis implantations. More particularly, the invention relates to a cylindrical threaded and pointed pin to be inserted by screwing into a bone tunnel (artificual bone alveolus) of the same diameter as the stem of the pin.

It is known to use endosseous screws for implantations in dentistry for anchoring superstructures such as individual dental crowns or dental crowns assembled in bridges. As the screw of such implantations must be firmly anchored to the jaw-bone, the thread is usually made so as to project to quite a large extent from the stem of the threaded pin and this results in excessive pressure being exerted on the jaw-bone with consequent risks of expulsion known to one skilled in the art.

It is an object of the present invention to provide a cylindrical threaded and pointed pin for implantation use in dentistry, which eliminates or reduces the aforementioned drawbacks of the conventional implantations, particularly with regard to the preservation of the integrity of the jaw-bone.

The external thread of the pin is formed of a thin spiral blade that winds helically around the outside of the cylindrical pin and has the purpose of permitting the pin to be inserted by screwing without exerting pressure on the surrounding bone. Thus, any damage that may be caused to the jaw-bone by the insertion of conical threaded products is avoided.

The pin may have various diameters provided that it is inserted by screwing into corresponding bone tunnels made by milling cutters of the same diameter as the cylindrical stem of the pin.

If desired, the pin may be provided with a stub that is slidable along the cylindrical body thereof and projects from the plane of the bone. This stub can then be locked in some way at the desired height along the setm of the pin to facilitate the construction of the actual prosthesis, reduce the consumption of material, favor the parallism and setting of the imprint and simplify the dental procedures.

SUMMARY OF THE INVENTION

These and other objects and advantages of the invention, which will become apparent from the following description, are achieved according to the invention by a cylindrical threaded and pointed pin for implantation use in dentistry, comprising an elongated cylindrical body provided with a head portion at one end, adapted to receive a screw wrench, and near the other end with a very thin and little projecting cylindrical external thread. The improvement over the prior art is achieved according to the invention due to the fact that the depth of the thread of the pin is about 1/10 of the diameter of the stem of the pin, the angle of the thread is about 35°, the pitch of the thread is about the same as the diameter of the stem of the pin and the latter is downwardly provided with a point the length of which is about the same as the outside diameter of the pin.

BRIEF DESCRIPTION OF THE DRAWINGS

FIG. 1 is an elevational view of a threaded pin for implantation use in dentistry according to the invention;

FIG. 2 is a top plan view of the pin of FIG. 1;

FIG. 3 is an enlarged sectional view of a detail of FIG. 1, and

FIG. 4 is a sectional view of a slidable stub that may be associated with the pin according to the invention.

DESCRIPTION OF PREFERRED EMBODIMENT

Referring to FIGS. 1 and 2, denoted by 1 is a cylindrical body 1 or stem of a pin for implantation use in dentistry according to the invention. The pin has an upper portion provided with a head 2 for the application of a screw wrench for screwing the pin into a jaw-bone. The pin is made of biocompatible material.

The lower portion of the pin is provided with an external thread 3 which permits the pin, when rotated, to advance into the jaw-bone.

A characteristic feature of this thread consists in that it is cylindrical, thin and "light", i.e. has a relatively small depth so as not to exert pressure on the jaw-bone as the pin is screwed in, although it ensures the pin to advance into the depth of the jaw-bone and the implantation to be securely fixed therein.

The pin terminates with a point having a shape corresponding to that of the bit of the milling cutter with which the bone tunnel is made, so that after the advance movement of the pin has come to an end, the pin will be located exactly within the bone tunnel.

FIG. 3 shows, on a larger scale, a detail of the threaded pin to permit a better understanding of the essential characteristics of the invention. These characteristics substantially consist in that the depth h of the threads is about 1/10 of the diameter d of the stem of the pin, the thread angle $\alpha$ is 35°, the pitch p is preferably the same as the diameter d of the stem of the pin and the length of the point 4 is about the same as the outside diameter D of the pin.

When the pin is made with these characteristics, it will accurately enter the corresponding bone seat made by the milling cutter and due to the light thread will be received therein without exerting pressure on the jaw-bone.

Thus, a safe fixing of the pin is obtained and the integrity of the jaw-bone is maintained.

FIG. 4 shows in a longitudinal section a slidable stub 5 which is provided with an axial hole 6 having a diameter corresponding to the diameter d of the stem 1 of the pin on which it may be mounted and locked in position to facilitate the construction of the actual prosthesis.

Obviously the overall length of the threaded pin and the number of turns of the thread may be varied as required or desired.

Although a preferred embodiment of the invention has thus been described in detail and illustrated in the accompanying drawings, it is to be understood that the invention is not limited to this precise embodiment and that numerous changes and modifications obvious to one skilled in the art may be made therein without departing from the scope of the invention as defined by the appended claims.

What is claimed is:

1. In a cylindrical threaded pin for implantation use in dentistry for insertion in a bone tunnel made by a pointed milling cutter in a jaw-bone, said pin comprising an elognated cylindrical stem provided with a head at one end thereof and with an external thread upon said stem at a second end thereof, said stem being of a diameter to fit within the bone tunnel, the improvement wherein the depth of said thread is substantially 1/10 of the diameter of said stem;

the included angle of said thread is substantially 35° defining a cutting thread for threading into and retainingly engaging the jawbone;

the pitch of said thread is substantially the same as the diameter of said stem;

and a downwardly extending point at said second end having a shape corresponding to the bit of said milling cutter.

2. A cylindrical threaded pin as defined in claim 1, and a stub having an axial bore slidably mounted on said stem and having a diameter corresponding to the diameter of said stem.

3. A cylindrical threaded pin as defined in claim 1, wherein the length of said point is substantially the same as the outside diameter of said pin.

* * * * *